(12) United States Patent
Koshoubu et al.

(10) Patent No.: US 7,492,460 B2
(45) Date of Patent: *Feb. 17, 2009

(54) ATTENUATED-TOTAL-REFLECTION MEASUREMENT APPARATUS

(75) Inventors: Jun Koshoubu, Hachioji (JP); Noriaki Soga, Hachioji (JP)

(73) Assignee: Jasco Corporation, Hachioji-shi, Tokyo (JP)

( * ) Notice: Subject to any disclaimer, the term of this patent is extended or adjusted under 35 U.S.C. 154(b) by 173 days.

This patent is subject to a terminal disclaimer.

(21) Appl. No.: 11/337,817

(22) Filed: Jan. 23, 2006

(65) Prior Publication Data
US 2006/0164633 A1 Jul. 27, 2006

(30) Foreign Application Priority Data
Jan. 25, 2005 (JP) ............................. 2005-016439

(51) Int. Cl.
*G01N 21/55* (2006.01)
(52) U.S. Cl. ..................................................... 356/445
(58) Field of Classification Search ....................... None
See application file for complete search history.

(56) References Cited
U.S. PATENT DOCUMENTS
3,705,755 A * 12/1972 Baer ........................... 359/202

6,141,100 A 10/2000 Burka et al.
7,224,460 B2 * 5/2007 Soga et al. ................... 356/444

OTHER PUBLICATIONS

Japanese Patent Abstract Publication No. 04-348254 published Dec. 3, 1992, Application No. 03-186804, filed Jul. 1, 1991, one page.

* cited by examiner

*Primary Examiner*—Gregory J Toatley, Jr.
*Assistant Examiner*—Amanda H Merlino
(74) *Attorney, Agent, or Firm*—Rankin, Hill & Clark LLP

(57) ABSTRACT

The present invention provides an attenuated-total-reflection ("ATR") measurement apparatus that collects light onto a contact surface between a sample and an ATR prism at an incident angle greater than or equal to a critical angle and measures total-reflection light from the contact surface. The attenuated-total-reflection measurement apparatus according to the invention includes: a light-irradiating system for emitting the light which is collected onto the contact surface; a photodetector for detecting the total-reflection light from the contact surface; an aperture for restricting the light which the photodetector detects to only light from a specific measurement site in the contact surface; and a detection-side scanning mirror provided in a light path extending from the ATR prism to the aperture.

6 Claims, 7 Drawing Sheets

FIG.2
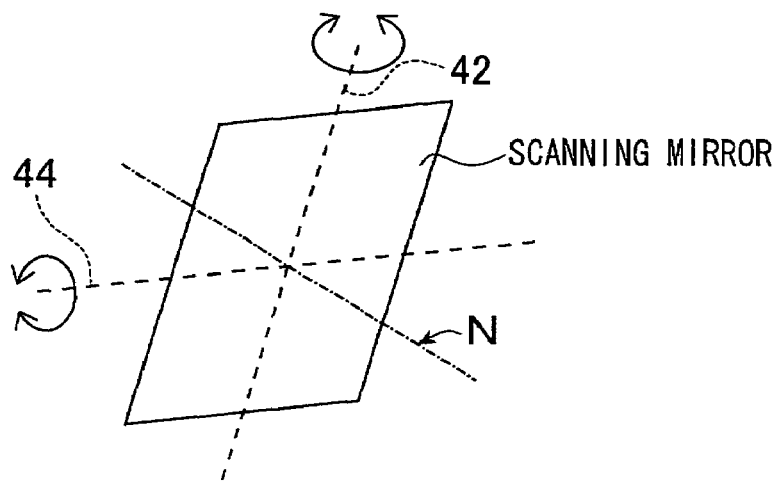
FIG.3
FIG. 3A
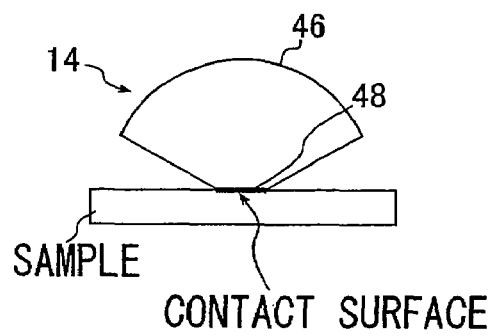
FIG. 3B
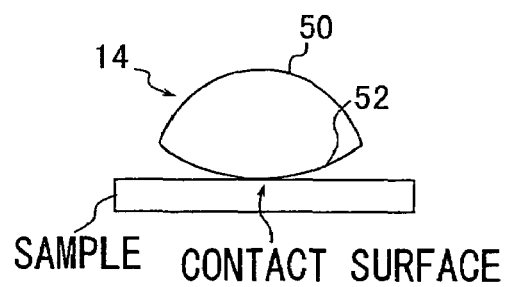

ATTENUATED-TOTAL-REFLECTION MEASUREMENT APPARATUS

RELATED APPLICATIONS

This application claims priority to the Japanese Patent Application 2005-16439 dated on Jan. 25, 2005 and is hereby incorporated with reference for all purposes.

BACKGOUND OF THE INVENTION

1. Field of the Invention

The present invention relates to attenuated-total-reflection measurement apparatuses, and more particularly, to an improved mapping mechanism thereof.

2. Description of the Related Art

Attenuated total reflection (ATR) is a measurement technique in which an ATR prism, which is a medium having a high refractive index, is placed in close contact with the surface of a sample to be measured. That is, under total-reflection conditions at the interface between the sample and the prism, light is incident on the surface of the sample via the ATR prism, and reflected light is measured. During total reflection, the light slightly penetrates into the sample surface, and some absorption occurs in a vicinity of the sample surface. By measuring the spectrum of this absorption, it is possible to obtain information about the surface region of the sample (see Japanese Unexamined Patent Application Publication No. H4-348254).

By attaching an ATR prism to the objective mirror of an infrared microscope, attenuated-total-reflection measurement of a minute site can be performed. Conventionally, however, such ATR measurement is performed at a single point using a single-element detector, and therefore, to measure a surface distribution, it is necessary to repeatedly remove the ATR prism from the sample and re-attach it. This results in problems, such as positional error of the prism, contamination at the contact surface of the prism when attaching it to the sample, and so forth, which are undesirable for high-speed, high-precision mapping measurement.

In the measurement described above, because light from the central part of the contact surface is received by the single-element detector, it is difficult to carry out mapping measurement with a spatial resolution below the size of the contact surface between the ATR prism and the sample (normally, the diameter of this region is about 100 µm). In other words, to perform mapping measurement at a level below the size of the contact surface, the position where the ATR prism contacts the sample surface should be slightly shifted, and the prism should be reattached at substantially the same position. However, it is difficult to minutely change the position of the prism, and in addition, reattaching the prism at the position where the prism and sample were in contact is disadvantageous from the point of view of measurement. If the size of the contact surface is reduced, the contact pressure from the prism on the sample becomes high.

In order to solve these problems, an imaging ATR measurement apparatus using a two-dimensional multi-element detector is disclosed in U.S. Pat. No. 6,141,100. Imaging measurement is performed by acquiring total-reflection light from a contact surface between an ATR prism and a sample using the two-dimensional multi-element detector. More specifically, the data from each individual element of the two-dimensional multi-element detector is associated with total-reflection light data from each position in the contact surface. However, a two-dimensional multi-element detector such as the focal plane detector array (FPA) disclosed in U.S. Pat. No. 6,141,100 has the following problems: (1) the cost is high; (2) because signals are read out from the elements in a serial fashion, it takes some time to complete acquisition of all data; (3) the measurement wavelength range is limited; and (4) defects occur in some of the elements in the light-receiving surface when fabricating the photodetector. Therefore, there is a demand for an apparatus that can perform ATR mapping measurement using a standard low-cost single-element detector or linear-array detector, without repeatedly separating and recontacting the prism and the sample.

SUMMARY OF THE INVENTION

The present invention has been conceived in light of the problems described above, and an object thereof is to provide an attenuated-total-reflection measurement apparatus that can perform high-speed, high-resolution two-dimensional mapping measurement, even when using a single-element detector or a linear-array detector.

An attenuated-total-reflection measurement apparatus of the present invention collects light onto a contact surface between a sample and an ATR prim at an incident angle greater than or equal to a critical angle and measures total-reflection light from the contact surface. The attenuated-total-reflection measurement apparatus of the present invention comprises: a light-irradiating system for emitting the light which is collected onto the contact surface; a photodetector system for detecting the total-reflection light from the contact surface; an aperture for restricting the light which the photodetector system detects to only light from a specific measurement site in the contact surface; and a detection-side scanning mirror provided in a light path extending from the ATR prism to the aperture. The detection-side scanning mirror is configured to allow the orientation of a reflecting surface thereof to be changed. And the measurement site in the contact surface, which is to be measured with the photodetector system, is changed by moving the reflecting surface of the detection-side scanning mirror with respect to the total-reflection light from the contact surface, to perform mapping measurement in the contact surface.

In the attenuated-total-reflection measurement apparatus according to the present invention, it is preferable that the attenuated-total-reflection measurement apparatus further comprises an irradiation-side scanning mirror for guiding the light from the light-irradiating system to the ATR prism. The irradiation-side scanning mirror is configured to allow the orientation of a reflecting surface thereof to be changed. And the irradiated position on the contact surface is changed by moving the reflecting surface of the irradiation-side scanning mirror with respect to the irradiation light from the light-irradiating system.

In the attenuated-total-reflection measurement apparatus according to the present invention, it is preferable that the attenuated-total-reflection measurement apparatus further comprises a controller for controlling the orientation of the reflecting surface of the detection-side scanning mirror.

In the attenuated-total-reflection measurement apparatus according to the present invention, it is preferable that the attenuated-total-reflection measurement apparatus further comprises a controller for controlling the orientation of the reflecting surface of the irradiation-side scanning mirror.

In the attenuated-total-reflection measurement apparatus according to the present invention, it is preferable that the attenuated-total-reflection measurement apparatus further comprises a microscope optical system for collecting light onto the contact surface and for collecting light from the contact surface.

In the attenuated-total-reflection measurement apparatus according to the present invention, it is preferable that the photodetector system is formed of a single-element detector.

In the attenuated-total-reflection measurement apparatus according to the present invention, it is preferable that the photodetector system is formed of a one-dimensional multi-element detector.

According to the present invention, a detection-side scanning mirror whose reflecting surface can be changed in orientation is provided, and a measurement site in the contact surface between a sample and an ATR prism is changed by changing the orientation of this reflecting surface. Therefore, it is possible to perform high-speed, high-precision two-dimensional mapping measurement even when using a single-element detector or a one-dimensional multi-element detector.

Furthermore, according to the present invention, an irradiation-side scanning mirror whose reflecting surface can be changed in orientation is provided, and an irradiation site in the contact surface between a sample and an ATR prism is changed by changing the orientation of this reflecting surface. Therefore, a measurement site can be efficiently radiated with light.

BRIEF DESCRIPTION OF THE DRAWINGS

FIG. 2 is a diagram depicting a scanning mirror in the present embodiment.

FIGS. 3A and 3B are sectioned diagrams showing examples of ATR prisms used in the present embodiment.

DESCRIPTION OF THE PREFERRED EMBODIMENT

Figure 1:
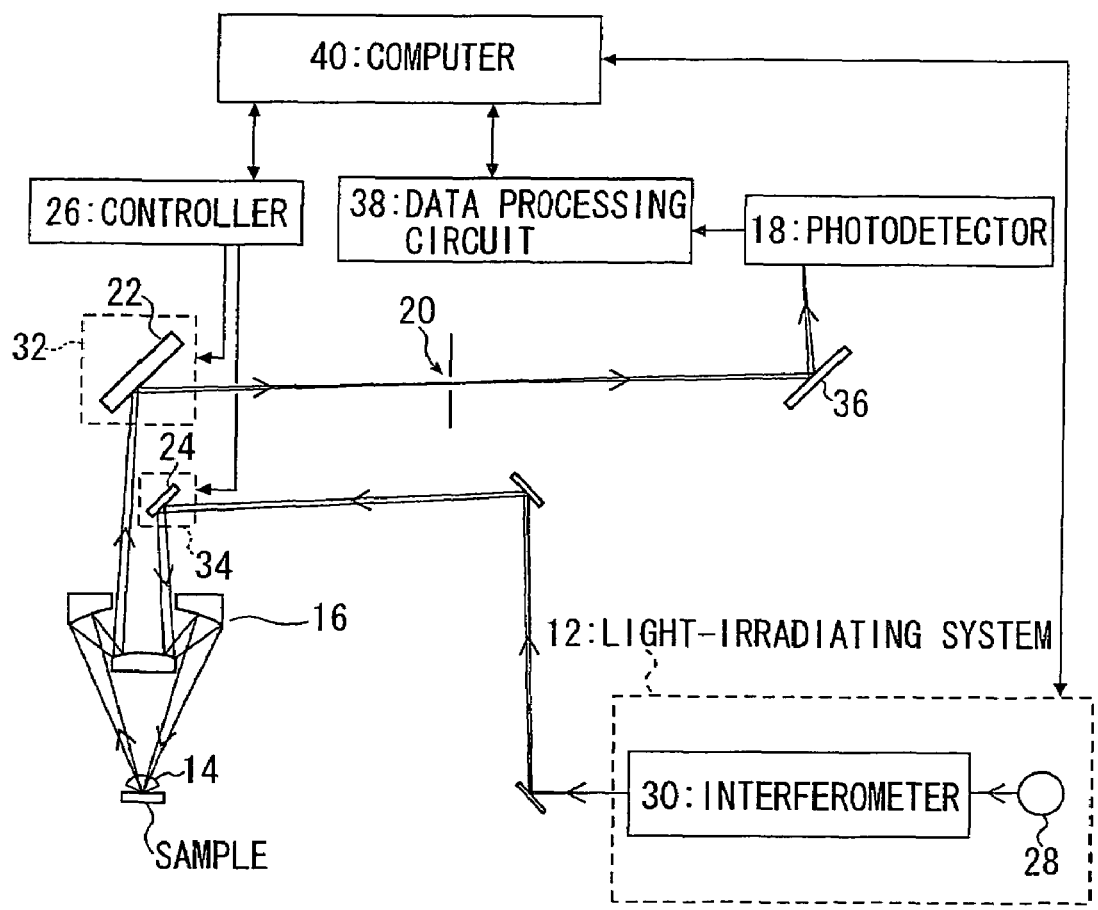
FIG. 1 is an outlined diagram showing the configuration of an attenuated-total-reflection measurement apparatus according to an embodiment of the present invention.

A preferred embodiment of the present invention will be described below with reference to the drawings. FIG. 1 is an outlined diagram of an attenuated-total-reflection measurement apparatus 10 according to the embodiment of the present invention. The attenuated-total-reflection measurement apparatus 10 of this embodiment includes a light-irradiating system 12; an ATR prism 14 that contacts a sample surface; an objective mirror (microscope optical system) 16 for collecting light onto the contact surface between the sample and the ATR prism 14 and for collecting light reflected from the contact surface; a photodetector (photodetector system) 18 for detecting the reflected light; an aperture 20 for restricting the light traveling towards the photodetector 18 to light emanating from a specific position in the contact surface; a detection-side scanning mirror 22 positioned in the light path extending from the ATR prism 14 to the aperture 20; and an irradiation-side scanning mirror 24 positioned in the light path extending from the light-irradiating system 12 to the ATR prism 14.

Light radiated from the light-irradiating system 12 is reflected by the irradiation-side scanning mirror 24 and is sent to the objective mirror 16, which is configured as a Cassegrainian lens or the like. From the objective mirror 16, the light is irradiated, via the ATR prism 14, onto a specific minute site in the contact surface between the ATR prism 14 and the sample, at an incident angle equal to or greater than the critical angle. At this time, the orientation of the reflecting surface of the irradiation-side scanning mirror 24 is controlled by a controller 26 so that the irradiated site matches the specific site. The total-reflection light from the sample passes through the ATR prism 14, is collected again by the objective mirror 16, and is sent to the detection-side scanning mirror 22. The total-reflection light from the sample is reflected at the detection-side scanning mirror 22 and is sent to the aperture 20. The orientation of the reflecting surface of the detection-side scanning mirror 22 is adjusted so that only light from the specific measurement site is directed towards the opening of the aperture 20. Reflected light from positions outside the measurement site is blocked at the aperture 20, and only light from the measurement site passes therethrough. The light passing through the aperture 20 is collected by a collective mirror 36 and is detected at the photodetector 18. The detected data is processed in a data processing circuit 38 and is stored in a computer 40. Thus, by changing the orientations of the reflecting surfaces of the irradiation-side scanning mirror 24 and the detection-side scanning mirror 22 and repeating the measurement described above, two-dimensional mapping measurement of the contact surface area between the ATR prism 14 and the sample is performed.

The above is an outline of the configuration of the present invention; next, each element constituting the present embodiment shall be described. The light-irradiating system 12 is formed of an infrared light source 28 and an interferometer 30. Light from the infrared light source 28 becomes interference light upon passing through the interferometer 30. And the interference light is then directed towards the irradiation-side scanning mirror 24. Although an example using a Fourier-transform spectrometer is shown in the present embodiment, a dispersion spectrometer may also be used. Furthermore, although the spectrometer is disposed at the light-irradiating system 12 side in the example shown here, it may be disposed at the photodetector 18 side.

The irradiation-side scanning mirror 24 is configured such that the orientation of the reflecting surface thereof can be changed, and therefore, the orientation of the reflecting surface with respect to the beam from the light-irradiating system 12 can be changed. As a result, the image position of the beam from the light-irradiating system 12 in the contact surface between the ATR prism 14 and the sample can be moved.

Similarly, the detection-side scanning mirror 22 is configured such that the orientation of the reflecting surface thereof can be changed, and therefore, it is possible to change the orientation of the reflecting surface of the detection-side scanning mirror 22 with respect to the incident direction of the light from the contact surface. Accordingly, setting the orientation of the reflection plane of the detection-side scanning mirror 22 determines from which position on the contact surface comes light passing through the aperture 20. In other words, the conjugate position of the aperture 20 on the contact surface can be changed.

Changing the orientations of the reflecting surfaces of the detection-side scanning mirror 22 and the irradiation-side scanning mirror 24 is achieved by means of driving mechanisms 32 and 34. The amounts of motion of the driving mechanism 32 and 34 are controlled by the controller 26. To change the orientations of the reflecting surfaces, for example, the mirrors should be designed to be capable of rotation about two mutually independent axes (that is, not parallel to each other). More specifically, as shown in FIG. 2, the scanning mirrors are made to rotate about orthogonal rotation axes 42 and 44 by the driving mechanisms. The driving mechanisms may be formed of stepper motors, piezoelectric elements, magnetostrictors, or the like. The amounts of rotation and the rotation directions produced in the scanning mirrors 22 and 24 by the driving mechanisms 32 and 34 are controlled by the controller 26. The relationship between the irradiation (or measurement) position and the orientation of the reflecting surface is stored in advance in the computer 40, and the controller 26 adjusts the amount of rotation and so forth based on that information. Accordingly, since it is possible to precisely control the normal N direction of the reflecting surface of the mirror, the reflection direction thereof with respect to the light incident on the mirror can be precisely controlled. Although the case of two rotation axes has been described here, when the irradiation position and the measurement position should be changed in only one direction, such as when using a one-dimensional multi-element detector, the mirrors may have only one rotation axis.

As the ATR prism 14, as shown in FIG. 3A, a prism having a hemispherical surface 46 (light entrance/exit surface) opposite the surface contacting the sample and an inverted trapezoidal shape (the short edge of the trapezoid is a contact surface 48) at the surface contacting the sample may be used. That is, a prism in which the sample contact surface 48 protrudes is used. Alternatively, as shown in FIG. 3B, a prism having a shape substantially like a convex lens, which is described in U.S. Pat. No. 6,141,100, wherein two opposing surfaces 50 and 52 have different radii and centers of curvature, may be used. The ATR prism used in the present invention, however, is not limited to these shapes. Furthermore, the material of the ATR prism is generally Ge, ZnSe, diamond, and so forth.

The aperture 20 is configured to allow the size and shape of the opening to be changed so as to enable adjustment of the range of the measurement site. The aperture 20 blocks reflected light and total-reflection light from regions outside the measurement site and selectively allows only light from the measurement site to pass therethrough. Thus, among the reflected light and the total-reflection light from the sample, the portion that is directed towards the opening of the aperture 20 is controlled by the detection-side scanning mirror 22. Therefore, by selecting the light that the photodetector 18 receives using the aperture 20, it is possible to perform measurement of a minute site on the sample with superior precision.

As the photodetector 18, a single element or one-dimensional multi-element detector normally used for infrared measurement may be used, for example, an MCT detector and an InSb detector.

The computer 40 is connected to the data processing circuit 38, the light-irradiating system 12, the controller 26, and other devices and performs device control, data processing and storage, and so forth. Also, for performing mapping-measurement, the measurement data is stored in the computer 40 in association with position information of the measurement site. The position information of the measurement site is obtained from the orientations of the reflecting surfaces of the scanning mirrors when acquiring the measurement data.

The present embodiment has been described in terms of a configuration in which both the detection-side scanning mirror and the irradiation-side scanning mirror are provided; however, if the irradiation position is fixed, the irradiation-side scanning mirror is not necessary. Since the irradiation intensity decreases as the measurement position deviates from the center of irradiation, it is preferable to also change the irradiation position at the same time using the irradiation-side scanning mirror, as described in the embodiment above.

Figure 4:
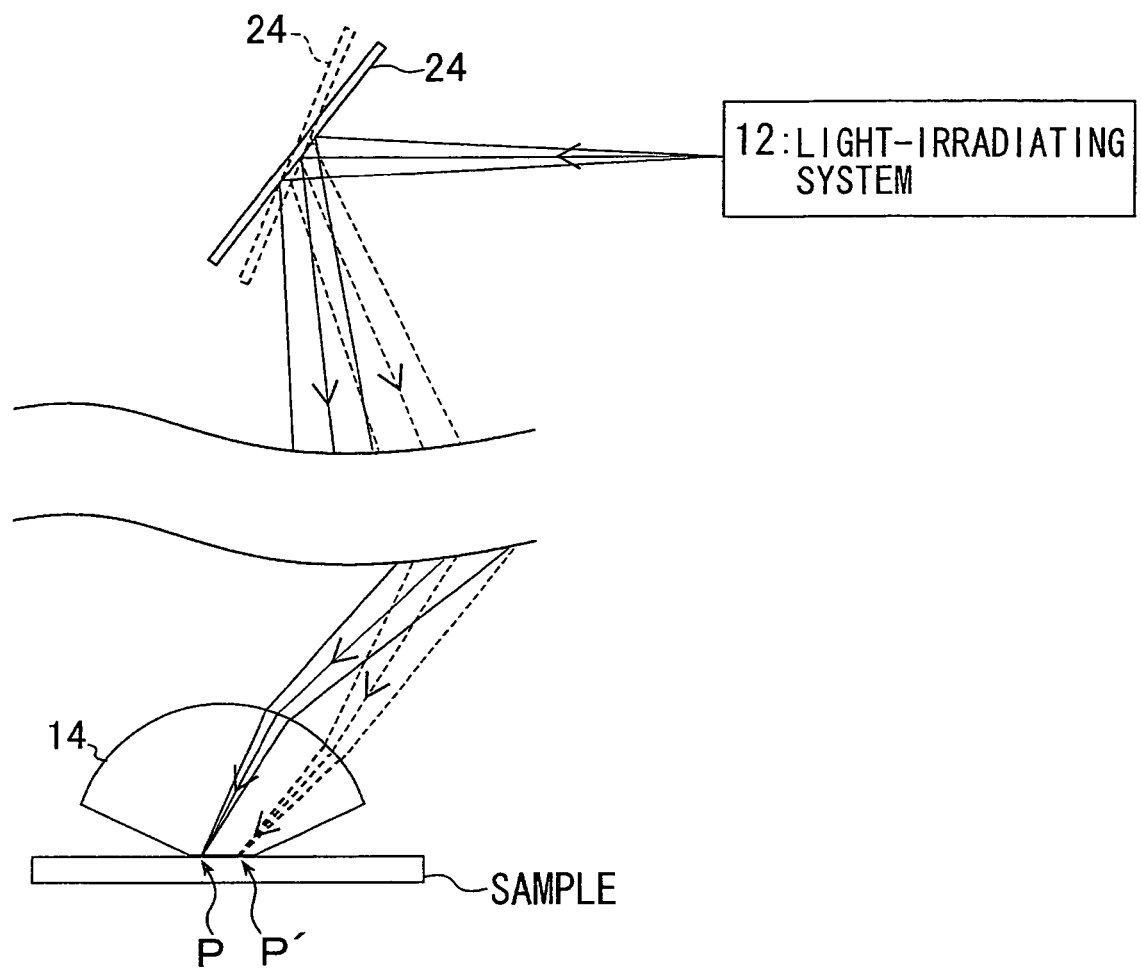
FIG. 4 is a diagram depicting the operation of an irradiation-side scanning mirror.

Next, the operation of the present embodiment will be described. FIG. 4 is a diagram depicting a case where the light irradiation position is changed using the irradiation-side scanning mirror 24. The mirror orientation and the beam are indicated by solid lines when the irradiation position is at reference character P, and by dotted lines when the irradiation position is at reference character P'. The light emitted from the light-irradiating system 12 is reflected by the irradiation-side scanning mirror 24, collected by the objective mirror (not shown in the drawing), and irradiated onto a specific site on the contact surface between the ATR prism 14 and the sample. At this time, the direction of propagation of the light incident on the ATR prism 14 changes depending on the orientation of the reflecting surface of the irradiation-side scanning mirror 24, and therefore, the irradiation position on the contact surface also changes. Accordingly, by changing the orientation of the irradiation-side scanning mirror 24, it is possible to readily change the irradiation position on the sample.

Figure 5:
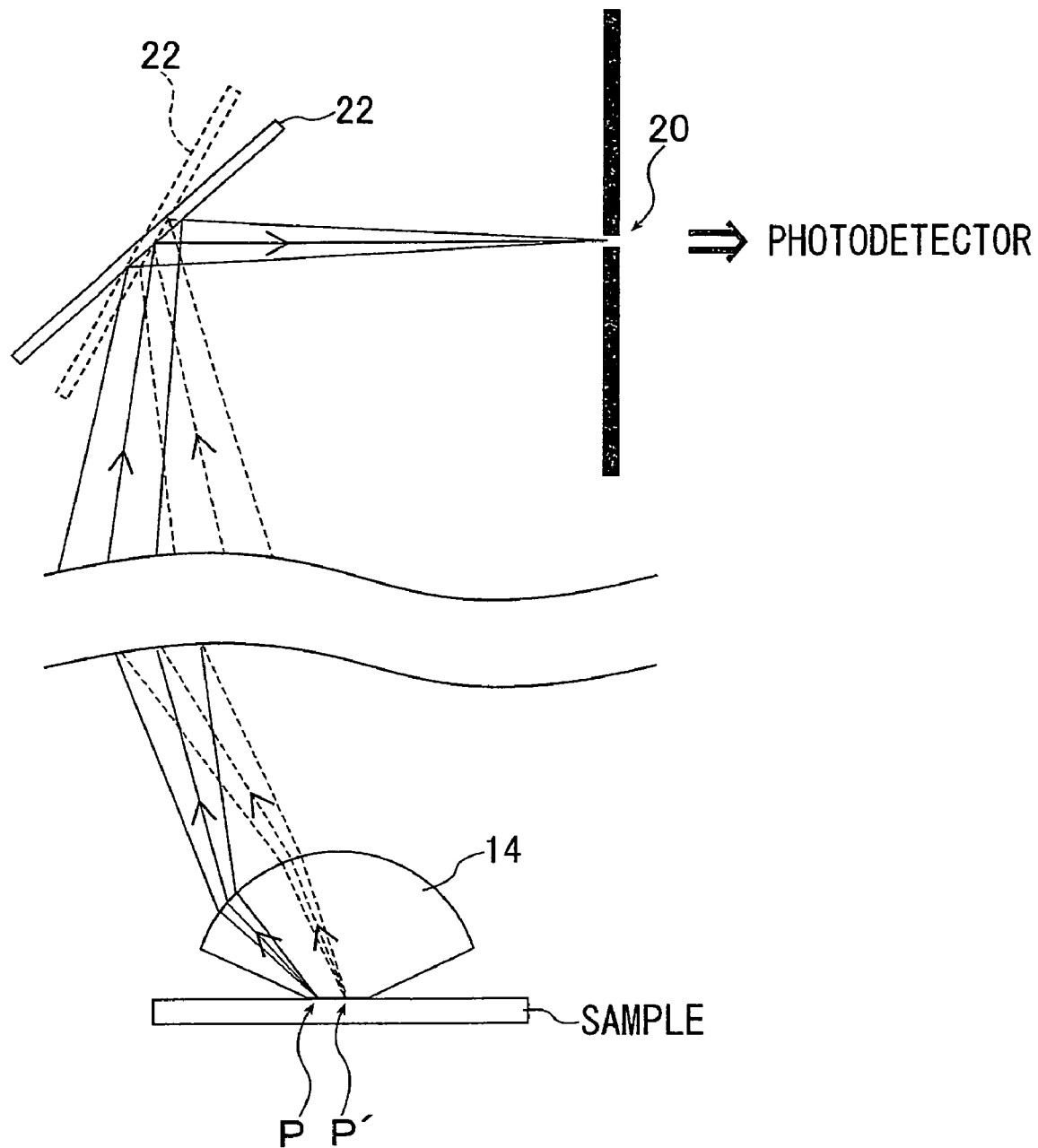
FIG. 5 is a diagram depicting the operation of a detection-side scanning mirror.

FIG. 5 is a diagram depicting a case where the measurement site is changed using the detection-side scanning mirror 22. The mirror orientation and beams are indicated by solid lines when the measurement site is located at reference character P, and by dotted lines when the measurement site is located at reference character P'. The light coming from the contact surface between the sample and the ATR prism 14 is collected by the objective mirror (not shown in the drawing) and is directed towards the detection-side scanning mirror 22. At this time, the direction of propagation of the light from the contact surface depends on the position on the sample surface. Therefore, when the orientation of the reflecting surface of the detection-side scanning mirror 22 is fixed in a certain direction, only light from a specific position on the sample surface corresponding to that orientation of the reflecting surface passes through the aperture 20, and light from other positions is blocked. When the orientation of the mirror 22 is changed with respect to the light coming from the contact surface, light coming from a different measurement position is sent to the opening of the aperture 20 among the light coming from the contact surface. In other words, by changing the orientation of the detection-side scanning mirror 22, the conjugate position of the aperture 20 on the contact surface can be changed. Thus, it is possible to easily change the measurement site to be measured by the photodetector 18 without moving the sample itself.

Next, mapping measurement using the measurement apparatus according to the present embodiment will be described.

Figure 6A:
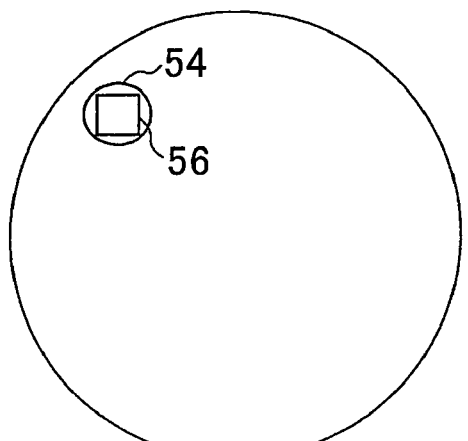
FIGS. 6A, 6B, and 6C are diagrams illustrating mapping measurement in a case where a single-element detector is used.
Figure 6B:
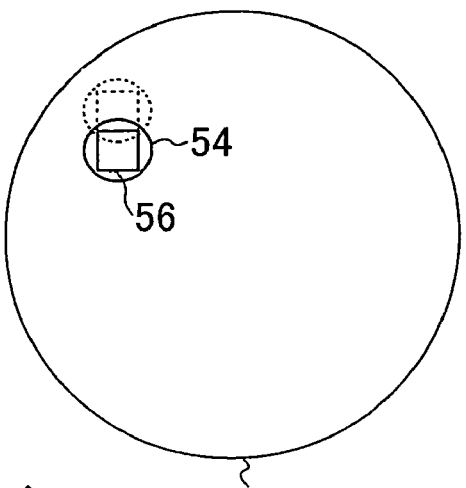
Figure 6C:
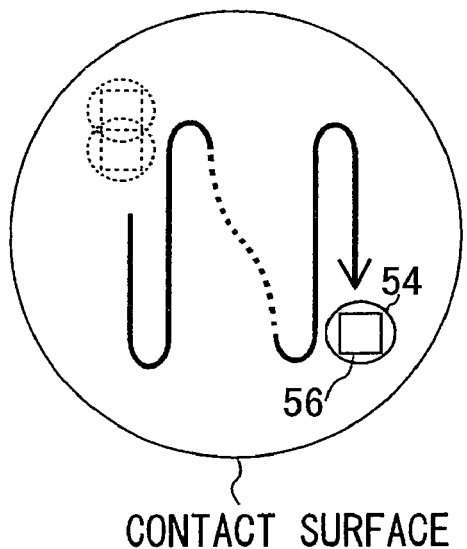

FIGS. 6A, 6B, and 6C are diagrams illustrating a mapping procedure. A case in which a single-element detector is used as the photodetector will be described. A circular part (reference numeral 54) in FIG. 6A to 6C is the irradiation site irradiated with measurement light, and a square part (reference numeral 56) is the measurement site to be measured by the photodetector. As shown in FIGS. 6A, 6B, and 6C (the parts indicated by dotted lines in the drawing indicate measurement and irradiation sites for which measurement has been completed), the irradiation site 54 is moved inside the contact surface (the region bounded by a large circle in FIG. 6A to 6C) between the ATR prism 14 and the sample by means of the irradiation-side scanning mirror 24. In association therewith, the measurement site 56 is moved by means of the detection-side scanning mirror 22 to perform mapping measurement in the contact surface between the ATR prism 14 and the sample.

Because the measurement site can be changed by means of the detection-side scanning mirror 22, it is possible to perform mapping measurement without repeatedly removing and re-attaching the prism 14, even when using a single-element detector. Therefore, it is possible to perform ATR mapping measurement at high speed and with high precision.

With the ATR technique, it is not necessary to perform sampling, unlike the standard transmission measurement technique, which simplifies the measurement procedure. Also, an improved spectrum with no saturated absorption peaks can be obtained. Furthermore, by using the ATR prism, it is possible to perform measurement with high magnification.

Figure 7A:
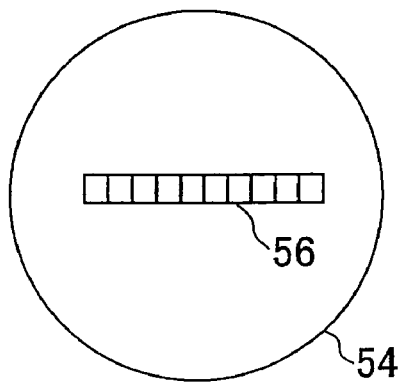
FIGS. 7A, 7B, and 7C are diagrams illustrating mapping measurement in a case where a linear-array detector is used.
Figure 7B:
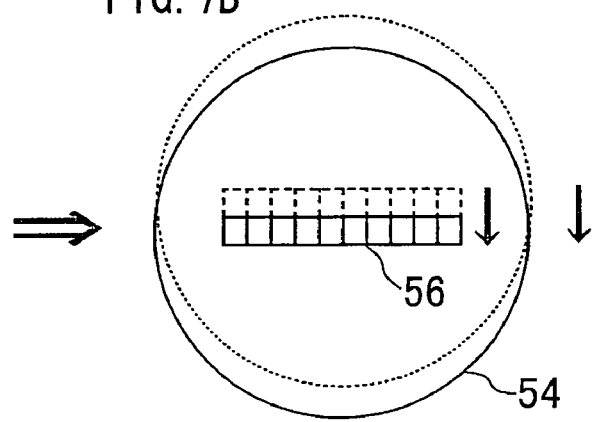
Figure 7C:
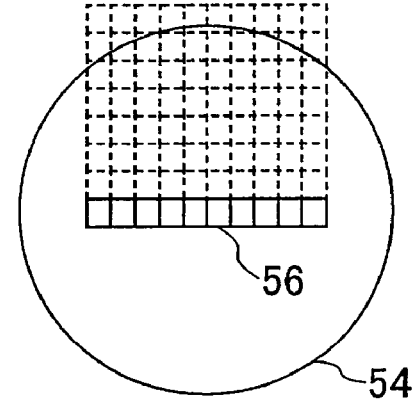

Next, a case in which a one-dimensional multi-element detector (linear-array detector) having photoreceiving elements arrayed in a row is used as the photodetector will be described. FIGS. 7A, 7B, and 7C are diagrams illustrating this case. In FIG. 7A, each grid square of the measurement site 56 corresponds to a photoreceiving element in the one-dimensional multi-element detector. Mapping measurement in the direction in which the photoreceiving elements are arrayed is performed all at once using the function of the photodetector itself. The region bounded by a circle in FIG. 7A shows the irradiation site (reference numeral 54). As shown in FIGS. 7A, 7B, and 7C, by changing the orientations of the detection-side and irradiation-side scanning mirrors 22 and 24, the measurement site (reference numeral 56) and the irradiation site (reference numeral 54) are sequentially moved in a direction orthogonal to the arrayed direction of the photoreceiving elements to perform measurement. The areas shown by dotted lines in FIGS. 7B and 7C indicate measurement sites and an irradiation site for which measurement has already been completed. As shown in FIG. 7C, by moving the measurement site in one direction, mapping measurement can be performed throughout the region where the prism and the sample make contact. Also, when using a one-dimensional multi-element detector, it is desirable to use a slit-shaped opening of the aperture to match the shape of the photoreceiver part of the detector.

By using such a one-dimensional multi-element detector, measurement can be carried out at a higher speed than in a case where a single-element detector is used, as shown in FIGS. 6A, 6B, and 6C. Because a linear detector can read out detection signals from elements in parallel, unlike an FPA, which is a two-dimensional detector, the measurement can be carried out at high speed.

Figure 8A:
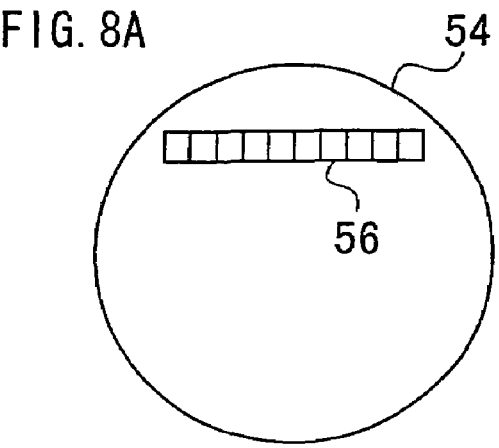
FIGS. 8A, 8B, and 8C are diagrams illustrating mapping measurement in a case where a linear-array detector is used.
Figure 8B:
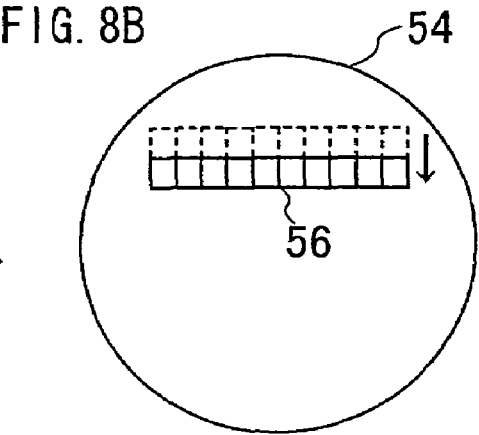
Figure 8C:
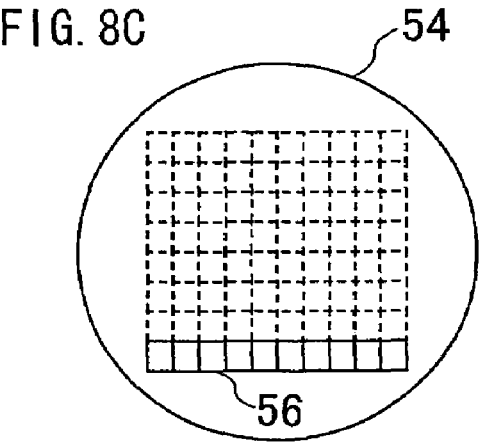

Although cases in which the irradiation site is moved in various ways have been described above, mapping measurement in an irradiated region may be carried out by making the site irradiated with measurement light sufficiently large and moving the measurement site within that irradiation region. More specifically, as shown in FIGS. 8A, 8B, and 8C, the diameter of the radiated beam is made sufficiently large, and the light is radiated in the region of the contact surface where mapping measurement is to be carried out. Thus, if the irradiation site (reference numeral 54) is fixed, the irradiation-side scanning mirror 24 is not necessary. Therefore, mapping measurement can be performed by moving only the measurement site (reference numeral 56) using the detection-side scanning mirror 22.

According to the attenuated-total-reflection measurement apparatus of the present embodiment, as described above, because the detection-side scanning mirror 22 whose reflecting surface can be changed in orientation is provided, it is possible to perform two-dimensional mapping measurement at high speed and with high precision, even when using a single-element detector or a one-dimensional multi-element detector. Furthermore, providing the irradiation-side scanning mirror 24 whose reflecting surface can be changed in orientation allows the measurement site to be efficiently radiated with light.

What is claimed is:

1. An attenuated-total-reflection measurement apparatus for collecting light onto a contact surface between a sample and an ATR prism at an incident angle greater than or equal to a critical angle and for measuring total-reflection light from the contact surface, comprising:
   light-irradiating system for emitting the light which is collected onto the contact surface;
   a photodetector system for detecting the total-reflection light from the contact surface;
   an aperture for restricting the light which the photodetector system detects to only light from a specific site in the contact surface, to set the specific site as a measurement site;
   a detection-side scanning mirror provided in a light path extending from the ATR prism to the aperture; and
   an irradiation-side scanning mirror for guiding the light from the light-irradiating system to the ATR prism;
   wherein the irradiation-side scanning mirror is configured to allow the orientation of a reflecting surface thereof to be changed independent of the detection-side scanning mirror, and the irradiated position on the contact surface is changed by moving the reflecting surface of the irradiation-side scanning mirror with respect to the irradiation light from the light-irradiating system, and
   wherein the detection-side scanning mirror is configured to allow the orientation of a reflecting surface thereof to be changed independent of the irradiation-side scanning mirror, and the measurement site in the contact surface, which is to be measured with the photodetector system, is changed by moving the reflecting surface of the detection-side scanning mirror with respect to the total-reflection light from the contact surface, to perform mapping measurement in the contact surface.

2. An attenuated-total-reflection measurement apparatus according to claim 1, further comprising:
   a controller for controlling the orientation of the reflecting surface of the detection-side scanning mirror.

3. An attenuated-total-reflection measurement apparatus according to claim 1, further comprising:
   a controller for controlling the orientation of the reflecting surface of the detection-side and irradiation-side scanning mirror.

4. An attenuated-total-reflection measurement apparatus according to claim 1, further comprising:
   a microscope optical system for collecting light onto the contact surface and for collecting light from the contact surface.

5. An attenuated-total-reflection measurement apparatus according to claim 1, wherein the photodetector system is formed of a single-element detector.

6. An attenuated-total-reflection measurement apparatus according to claim 1, wherein the photodetector system is formed of a one-dimensional multi-element detector.

* * * * *